(12) United States Patent
Tsukada et al.

(10) Patent No.: US 10,835,141 B2
(45) Date of Patent: Nov. 17, 2020

(54) WEARABLE ELECTRODE

(71) Applicants: NIPPON TELEGRAPH AND TELEPHONE CORPORATION, Tokyo (JP); TORAY INDUSTRIES, INC., Tokyo (JP)

(72) Inventors: Shingo Tsukada, Atsugi (JP); Nahoko Kasai, Atsugi (JP); Koji Sumitomo, Atsugi (JP); Hiroshi Nakashima, Atsugi (JP); Masanobu Sato, Tokyo (JP); Toru Arakane, Tokyo (JP); Yuri Hamano, Tokyo (JP); Takashi Teshigawara, Tokyo (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 0 days.

(21) Appl. No.: 15/577,696

(22) PCT Filed: Jul. 8, 2016

(86) PCT No.: PCT/JP2016/070271
§ 371 (c)(1),
(2) Date: Nov. 28, 2017

(87) PCT Pub. No.: WO2017/007017
PCT Pub. Date: Jan. 12, 2017

(65) Prior Publication Data
US 2018/0160928 A1  Jun. 14, 2018

(51) Int. Cl.
*A61B 5/0408*  (2006.01)
*A61B 5/00*  (2006.01)
(Continued)

(52) U.S. Cl.
CPC .......... *A61B 5/0408* (2013.01); *A61B 5/0416* (2013.01); *A61B 5/0478* (2013.01);
(Continued)

(58) Field of Classification Search
CPC ... A61B 5/6802; A61B 5/6804; A61B 5/6805; A61B 5/04; A61B 5/0402; A61B 5/0006;
(Continued)

(56) References Cited

U.S. PATENT DOCUMENTS 6,668,380 B2 * 12/2003 Marmaropoulos .. A61N 1/0484
2/69
7,395,106 B2 * 7/2008 Ryu ..................... A61B 5/6804
600/388

(Continued)

FOREIGN PATENT DOCUMENTS

CN      103930612 A    7/2014
CN      203914907 U    11/2014
(Continued)

OTHER PUBLICATIONS

Extended European Search Report in related application EP 16821485.6, ISA/EP, Munich, dated Oct. 26, 2018.
(Continued)

*Primary Examiner* — Eun Hwa Kim (57) ABSTRACT

A wearable electrode includes: a garment including an outer member and a backing member configured to cover at least a part of an inner surface of the outer member; and an electrode unit configured to come into contact with a living body clothed in the garment to acquire a biological signal emitted by the living body and attached to an opposite side of the backing member from the outer member, and a core wire which can be inserted into an accommodation section formed in the electrode unit. The outer member and the
(Continued)

backing member are connected to a part other than a part of the backing member, to which the electrode unit is attached.

5 Claims, 3 Drawing Sheets

(51) Int. Cl.
*A61B 5/0478* (2006.01)
*A61B 5/0416* (2006.01)

(52) U.S. Cl.
CPC .......... *A61B 5/6802* (2013.01); *A61B 5/6804* (2013.01); *A61B 5/0006* (2013.01); *A61B 2562/0209* (2013.01)

(58) Field of Classification Search
CPC ... A61B 5/0408; A61B 5/0478; A61B 5/0416; A61B 2562/0209
See application file for complete search history.

(56) References Cited

U.S. PATENT DOCUMENTS

| | | | |
|---|---|---|---|
| 7,966,052 B2* | 6/2011 | DeFusco | A61B 5/0245 600/386 |
| 8,506,350 B1 | 8/2013 | Silverman et al. | |
| 8,527,028 B2* | 9/2013 | Kurzweil | A61B 5/0408 600/382 |
| 2005/0034485 A1* | 2/2005 | Klefstad-Sillonville | A41D 13/1281 66/171 |
| 2007/0038057 A1 | 2/2007 | Nam et al. | |
| 2007/0073131 A1 | 3/2007 | Ryu et al. | |
| 2008/0287769 A1 | 11/2008 | Kurzweil et al. | |
| 2008/0287770 A1 | 11/2008 | Kurzweil et al. | |
| 2013/0041272 A1* | 2/2013 | Guillen Arredondo | A61B 5/02438 600/509 |
| 2013/0281816 A1 | 10/2013 | Strauss et al. | |
| 2014/0039292 A1 | 2/2014 | Su et al. | |
| 2014/0343392 A1 | 11/2014 | Yang | |
| 2015/0025354 A1 | 1/2015 | Salonius et al. | |
| 2015/0119677 A1* | 4/2015 | Liu | A61B 5/04085 600/389 |

FOREIGN PATENT DOCUMENTS

| | | |
|---|---|---|
| EP | 1506738 A1 | 2/2005 |
| EP | 2684516 A1 | 1/2014 |
| WO | WO-2012/088398 A2 | 6/2012 |

OTHER PUBLICATIONS

ANSI/AAMI EC12:2000/(R)2005, "Disposable ECG electrodes".
International Search Report for PCT/JP2016/070271, ISA/JP, Tokyo, dated Sep. 27, 2016, with translation.
Office Action for Chinese Application No. 201680036998.8; dated Nov. 29, 2019; 11 pp.
ANSI/AAMI EC12:2000 (R2010), "Disposable ECG electrodes".
International Search Report for PCT/JP2016/070267, ISA/JP, dated Oct. 4, 2016, with English translation attached.
Extended European Search Report in related Application EP16821484. 9, ISA/EP, Munich, dated Oct. 18, 2018.

* cited by examiner

WEARABLE ELECTRODE

CROSS REFERENCE TO RELATED APPLICATIONS

This application is a 371 U.S. National Stage of International Application No. PCT/JP2016/070271, filed Jul. 8, 2016, which claims the benefit of and priority to Japanese Patent Application No. 2015-137287, filed Jul. 8, 2015. The disclosures of the above applications are incorporated herein by reference.

TECHNICAL FIELD

The present invention relates to a wearable electrode.

BACKGROUND ART

Research and development of systems in which electrode units are attached to undergarment type garments worn by users (living bodies) and biological signals emitted by the users are acquired have been actively underway as effective tools of medical care health systems for aging populations. Hereinafter, an object constituted of electrode units and garments is referred to as a wearable electrode.

Wearable electrodes require variations in undergarments according to sex, body shape, seasonal adaptations, size development, age, and the like. However, the number of pharmacist certification numbers increases for the various variations, and procedures become complicated due to the various variations, that is, it becomes difficult to approve, manufacture, and manage wearable electrodes as medical instruments. For this reason, the various requirements or the like need to be dealt with using as few wearable electrode variations as possible.

Also, in medical wearable electrodes, electrode sections and wiring sections are determined by medical standards (for example, refer to Non-Patent Document 1).

DOCUMENTS OF THE PRIOR ART

Patent Document

Non-Patent Document 1

ANSFAAMI EC12:2000 (R2010), "Disposable ECG electrodes"

SUMMARY OF INVENTION

Problems to be Solved by the Invention

However, when a garment moves due to a motion or the like of a user, there is a problem in that an electrode unit moves and thus measurement cannot be stably performed.

The present invention was made in view of the above-described circumstances, and an objective thereof is to provide a wearable electrode in which movement of an electrode unit is suppressed even when a garment worn by a user moves.

Means for Solving the Problems

An aspect of the present invention is a wearable electrode including: a garment including an outer member and a backing member configured to cover at least a part of an inner surface of the outer member; an electrode unit configured to come into contact with a living body clothed in the garment to acquire a biological signal emitted by the living body and attached to an opposite side of the backing member from the outer member; and a core wire which is able to be inserted into an accommodation section formed in the electrode unit, wherein the outer member and the backing member are connected to a part other than a part of the backing member to which the electrode unit is attached.

As a preferred example, the wearable electrode may further include a core wire which is able to be inserted into an accommodation section formed in the electrode unit, and the electrode unit may include: a conductive layer configured to acquire the biological signal; a sandwiched layer disposed on one surface of the conductive layer and in contact with the conductive layer; and a pair of connection sections configured to connect the conductive layer and the sandwiched layer to extend in a reference direction along the one surface and disposed along the one surface and to be arranged in a direction intersecting the reference direction, wherein a part between the conductive layer and the sandwiched layer and between the pair of connection sections may constitute the accommodation section.

In this case, preferably, the distance between the pair of connection sections in the reference direction on a first side may be shorter than the distance between the pair of connection sections in the reference direction on a second side.

As a typical example, the conductive layer may be formed of a fiber structure impregnated with a conductive polymer, and the sandwiched layer may be formed of a metal.

As another typical example, a locking section may be fixed to the backing member, a first locked section locked to be attached to and detached from the locking section may be fixed to the electrode unit, and a second locked section locked to be attached to and detached from the locking section may be fixed to the core wire.

Advantageous Effects of the Invention

According to the present invention, a wearable electrode in which movement of an electrode unit is suppressed even when a garment worn by a user moves can be provided.

EMBODIMENTS FOR CARRYING OUT THE INVENTION

An embodiment of a wearable electrode according to the present invention will be described below with reference to FIGS. 1 to 4. Note that, in all of the following drawings, ratios of thicknesses or dimensions of constituent elements are adjusted for the sake of ease of viewing the drawings.

Figure 1:
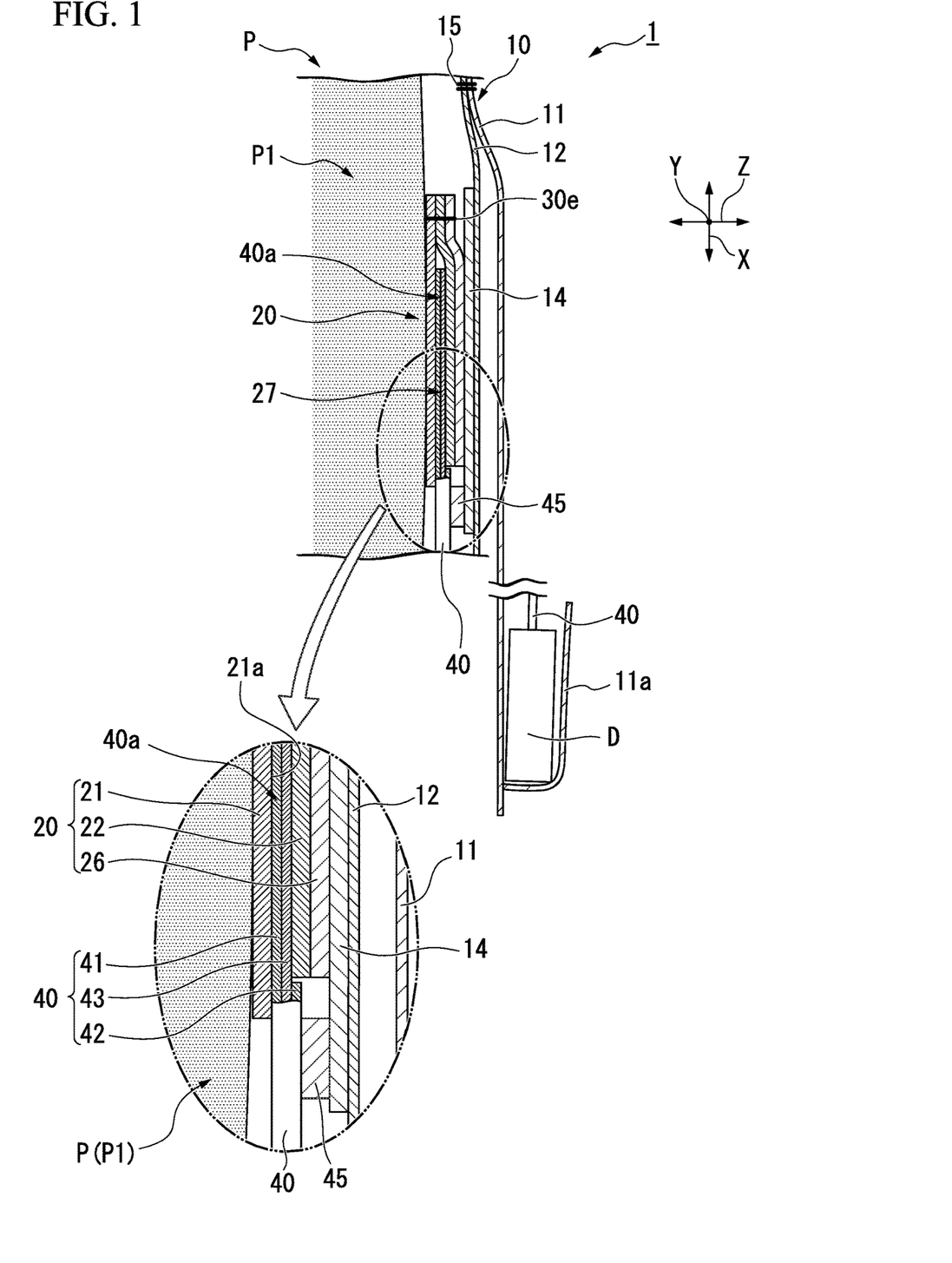
FIG. 1 is a vertical cross-sectional view of a front surface of a wearable electrode according to an embodiment of the present invention.
Figure 2:
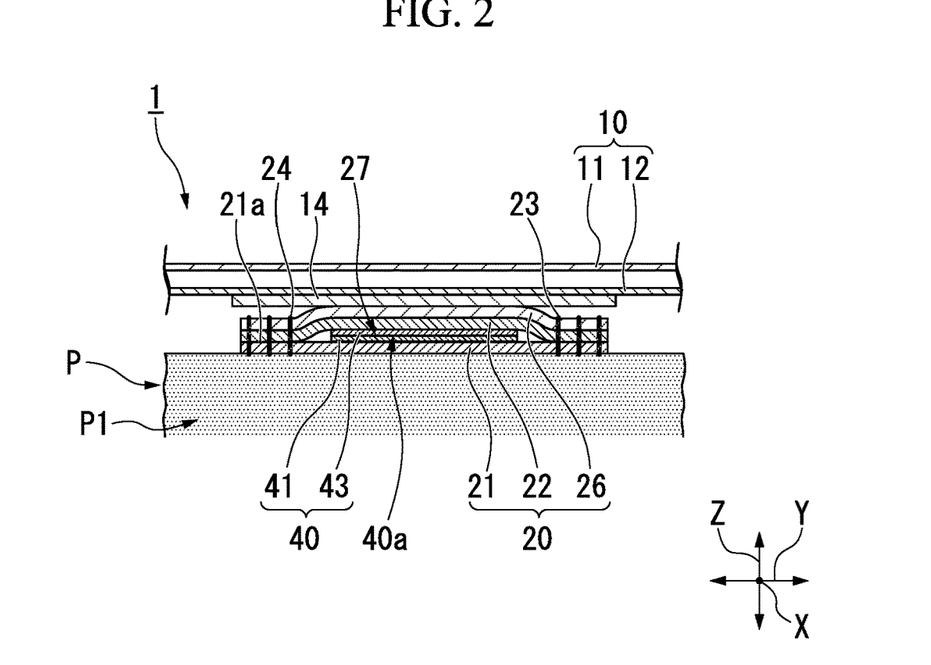
FIG. 2 is a horizontal cross-sectional view of a front surface of the wearable electrode.

As shown in FIGS. 1 and 2, a wearable electrode 1 according to the embodiment includes an undergarment (a garment) 10 having an outer member 11 and a backing member 12, an electrode unit 20 attached to an opposite side of the backing member 12 from the outer member 11, and a wiring section 40 connected to the electrode unit 20.

Note that FIG. 1 illustrates a state in which a standing user (a living body) P is clothed in the wearable electrode 1.

First, the electrode unit 20 will be described below.

Figure 3:
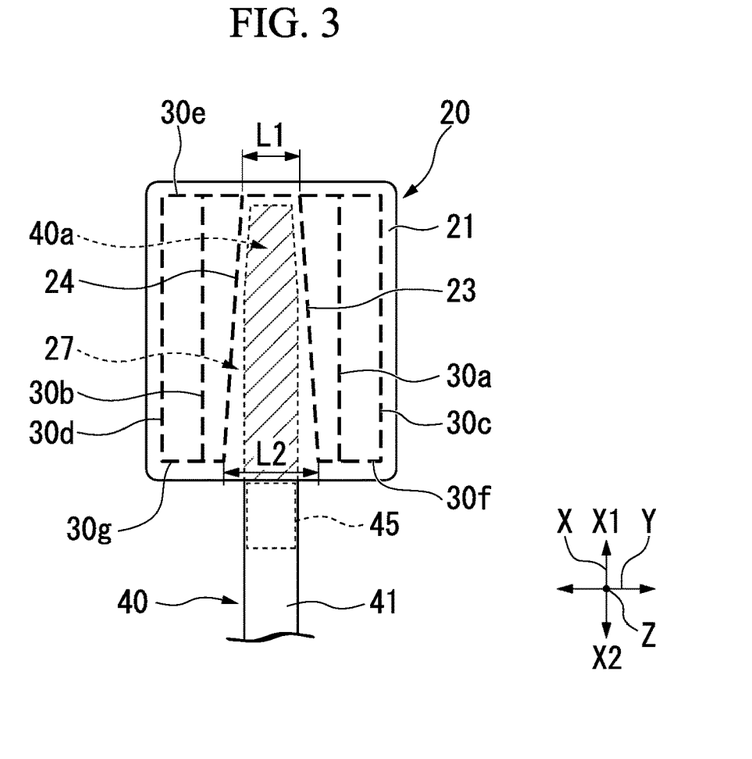
FIG. 3 is a bottom view of a biological electrode unit of the wearable electrode.

The electrode unit 20 acquires an electric biological signal emitted by the user P. As shown in FIGS. 1 to 3, the electrode unit 20 includes a conductive layer 21 configured to acquire a biological signal, a sandwiched layer 22 disposed on one surface 21a of the conductive layer 21, and a pair of connection sections 23 and 24 configured to connect the conductive layer 21 and the sandwiched layer 22 to extend in a reference direction X. The electrode unit 20 in this example is a type having a wide width.

The reference direction X is a direction along the one surface 21a of the conductive layer 21.

The conductive layer 21 is formed of a fiber structure impregnated with a conductive polymer.

Examples of a form of the fiber structure used for the conductive layer 21 include a woven fabric, a knitted fabric, or a nonwoven fabric. When the amount of conductive resins (conductive polymers) to be impregnated into the fiber structure is insufficient, since washing durability in repeated use is not obtained, a base weight of the fiber structure (a unit weight of a cloth impregnated with the conductive polymer) is preferably 50 g/m$^2$ or more and 300 g/m$^2$ or less. When the base weight is less than 50 g/m$^2$, the amount of the impregnated conductive resin decreases and thus washing durability cannot be obtained. When the base weight is more than 300 g/m$^2$, wearability is worse. The base weight is more preferably 60 g/m$^2$ or more and 250 g/m$^2$ or less.

The thickness of the fiber structure is preferably 0.2 mm or more and 2.0 mm or less. When the thickness is less than 0.2 mm, since the cloth is too thin, a substantial base weight decreases and thus the amount of the impregnated conductive resin decreases. When the thickness exceeds 2.0 mm, since the cloth is too thick, wearability is worse. The base weight is more preferably 0.3 mm or more and 1.5 mm or less.

Also, in order to continuously obtain good electrocardiographic waveforms, it is necessary to bring the conductive layer 21 into contact with skin and maintain an attached state. Since a cloth constituting a fiber structure needs to have flexibility in order for the conductive layer 21 to be continuously attached to skin, the fiber structure is preferably a woven fabric, a knitted fabric, or a nonwoven fabric, and more preferably a knitted fabric having higher flexibility. Here, when the conductive layer 21 is broken or moves during wear because the conductive layer 21 itself is too flexible, a member for reinforcement may be disposed on a back side of the conductive layer 21.

In addition, tissues and manufacturing methods of fiber structures represented by a knitted fabric are not particularly limited, but a shape of the conductive layer 21 is preferably a shape which retains moisture such as sweat and double knits can be preferably used as the knitted fabric. Examples of such tissues include double raschel tissues, cardboard tissues, reversible tissues, smooth tissues, milling tissues, fleeced tissues, and the like, but the present invention is not limited thereto.

A woven or knitted fabric used for the conductive layer 21 of the present invention preferably includes multifilament yarns composed of a plurality of monofilaments in view of supporting of a conductive resin in a fiber structure and high conductivity. Fineness of the multifilament yarns is not particularly limited, but the fineness thereof is preferably 30 dtex to 400 dtex in view of taking advantage of characteristics of the fiber structure. The mixing ratio of multifilament yarns in the woven or knitted fabric is not particularly limited as long as the mixing ratio does not affect performance of the fiber structure, but the mixing ratio thereof is preferably a higher mixing ratio in view of conductivity and durability and more preferably 50% or more and 100% or less.

Examples of materials of the multifilament yarn used for the woven or knitted fabric include polyester-based synthetic fibers such as polyethylene terephthalate, polytrimethylene terephthalate, and polybutylene terephthalate, and polyamide-based synthetic fibers such as nylon, and the like, but the present invention is not limited thereto. Furthermore, materials obtained by blending additives such as titanium oxide into the woven or knitted fabric may be used and fibers modified with polymers used to give functionality such as hygroscopicity improvement may also be used.

Also, cross-sectional shapes of unit monofilaments constituting multifilaments are not limited, and yarns with various different cross-sectional shapes represented by circular shapes, triangular shapes, octagonal shapes, flat shapes, and Y shapes can also be used. As non-elastic yarns, core sheaths or side-by-side type composite yarns composed of polymers with different viscosities can also be used. False twisted yarns obtained by performing false twisting on raw yarns may also be used. Synthetic fibers of polyacrylonitrile, polypropylene, and the like, regenerated fibers of rayon, polynosic, cupra, and the like, semisynthetic fibers of acetate, triacetate, and the like, and natural fibers represented by silk can be used.

The fiber structure according to the present invention preferably includes multifilaments composed of monofilaments with filament diameters of 0.2 dtex or less in view of supporting conductive resins on fiber surfaces and in voids between fibers. The mixing ratio of the monofilament multifilaments of 0.2 dtex or less in the fiber structure is not particularly limited as long as the mixing ratio does not affect performance of the fiber structure, but the mixing ratio is preferably a high mixing ratio in view of conductivity and durability and more preferably 50% or more and 100% or less.

In addition, as the number of monofilaments increases, voids formed by a plurality of monofilaments, that is, sizes of portions carrying conductive resins, decrease, so that performance of supporting conductive resins in a fiber structure increases and excellent high conductivity and washing durability can be obtained because continuity of conductive resins is maintained even when sizes of portions carrying conductive resins are decreased by decreasing filament diameters.

Microfibers with filament diameters of 5 μm or less used for artificial leathers, outer members, or the like are preferably used, and nanofibers with filament diameters of 10 nm or more and 1000 nm or less that have been used in recent years for the purpose of preventing slipping of linings of sports clothes, brassieres, golf gloves, and the like are more preferably used.

Fiber structures including nanofiber staple yarn assemblies prepared from "Nanoalloy (registered trademark)" fibers, monofilament yarn assemblies prepared using an electrospinning method and the like, and nanofibers prepared using a known method can be appropriately used as nanofibers, but fiber structures including multifilament yarns of nanofibers are more desirable.

The multifilament yarns of the nanofibers can be prepared using a known composite spinning method or the like.

For example, nanofiber multifilament yarns, in which variations in filament diameters are small, obtained by performing sea component removal treatment on composite fibers using a composite spinneret disclosed in Japanese Examined Patent Application, First Publication No. 2013-185283 can be effectively used, but the present invention is not limited thereto. Here, the sea component removal treatment refers to a process of melting sea components of fibers and leaving island components.

As the conductive polymers, conductive polymers containing a mixture of poly3,4-ethylenedioxythiophene and polystyrene sulfonic acid (PEDOT-PSS) can be appropriately used.

Besides this, examples of the conductive polymers include pyrrole-based, thiophene-based, isothianaphthene-based, phenylene-based, acetylene-based, and aniline-based conductive polymers, copolymers thereof, or the like. In addition, examples of dopants of the conductive polymers may be at least one type of ion of polymer ions such as halide ions, perchlorate ions, tetrafluoroborate ions, hexafluoroarsenate ions, sulfate ions, nitrate ions, thiocyanate ions, phosphate ions, trifluoroacetate ions, tosylate ions, alkylsulfonate ions, and polyacrylate ions.

The conductive layer 21 having the fiber structure according to the present invention has low irritation and high safety when in contact with skin. When a signal cannot be obtained satisfactorily due to drying of skin or the like, it is desirable to apply a small amount of physiological saline or humectant to the fiber structure. Examples of the humectant include glycerol, sorbitol, polyethylene glycol, polyethylene glycol-polypropylene glycol copolymers, ethylene glycol, sphingosine, phosphatidylcholine, and the like, and one of these may be independently used or two or more of these may be used in combination.

By moisturizing the conductive layer 21 as described above, when the conductive layer 21 comes into contact with skin of a user P, an adhesive force occurs due to wettability of the humectant.

The sandwiched layer 22 is formed of silver fabric cloth made of yarns coated with silver or fibers of a metal such as stainless steel. The resistivity of the sandwiched layer 22 is smaller than the resistivity of the conductive layer 21. The sandwiched layer 22 is electrically connected to the conductive layer 21 by coming into direct contact with the conductive layer 21.

An electrode-side male surface fastener (a first locked section) 26 locked to be attached to and detached from a female surface fastener 14, which will be described below, is fixed to a surface on an opposite side of the sandwiched layer 22 from the conductive layer 21. The electrode-side male surface fastener 26 has a harder hook surface than a loop surface of the female surface fastener 14.

Connection sections 23 and 24 correspond to stitches obtained by stitching the conductive layer 21, the sandwiched layer 22, and the electrode-side male surface fastener 26 using threads. The connection sections 23 and 24 are disposed along the one surface 21a away from each other in an intersecting direction (an intersecting direction) Y which intersects the reference direction X. The reference direction X and the intersecting direction Y are directions along the one surface 21a of the conductive layer 21. The connection sections 23 and 24 extend linearly but are inclined with respect to the reference direction X.

A distance L1 between the pair of connection sections 23 and 24 in a first side (one side) X1 of the reference direction X is shorter than a distance L2 between the pair of connection sections 23 and 24 in a second side (the other side) X2 of the reference direction X. The conductive layer 21 and the sandwiched layer 22 between the connection sections 23 and 24 are not connected to each other.

An accommodation section 27 is constituted of a part between the conductive layer 21 and the sandwiched layer 22 and between the pair of connection sections 23 and 24. The accommodation section 27 is formed in the electrode unit 20.

As shown in FIG. 3, auxiliary connection sections 30a to 30g are provided to connect the conductive layer 21, the sandwiched layer 22, and the electrode-side male surface fastener 26 to each other. The auxiliary connection sections 30a to 30g are constituted as stitches.

To be more specific, each of the auxiliary connection sections 30a and 30b extends in the reference direction X and is disposed to sandwich the connection sections 23 and 24 in the intersecting direction Y. Each of the auxiliary connection sections 30c and 30d extends in the reference direction X and is disposed to sandwich the auxiliary connection sections 30a and 30b in the intersecting direction Y.

The auxiliary connection sections 30e extends in the intersecting direction Y and is connected to an end portion of the auxiliary connection section 30c on the first side X1 in the reference direction X and an end portion of the auxiliary connection section 30d on the first side X1 in the reference direction X. The auxiliary connection section 30f extends in the intersecting direction Y and is connected to an end portion of the auxiliary connection section 30c on the second side X2 in the reference direction X and an end portion of the connection section 23 on the second side X2 in the reference direction X. The auxiliary connection section 30g extends in the intersecting direction Y and is connected to an end portion of the auxiliary connection section 30d on the second side X2 in the reference direction X and an end portion of the connection section 24 on the second side X2 in the reference direction X.

In other words, the auxiliary connection section 30f and the auxiliary connection section 30g are away from each other in the intersecting direction Y. The wiring section 40 is inserted into the accommodation section 27 from between the auxiliary connection section 30f and the auxiliary connection section 30g.

The outer member 11 and the backing member 12 of the undergarment 10 can be formed of a desired fabric or the like.

As shown in FIGS. 1 and 2, the backing member 12 covers at least a part of an inner surface of the outer member 11. A female surface fastener (a locking section) 14 is fixed to an opposite side of the backing member 12 from the outer member 11. The female surface fastener 14 has the softer loop surface than the hook surface of the electrode-side male surface fastener 26. The female surface fastener 14 is fixed to the backing member 12 using stitches or the like (not shown).

The female surface fastener 14 is preferably formed at a position at which it faces a chest P1 of the user P when the user P is clothed in the undergarment 10 of the wearable electrode 1.

The outer member 11 and the backing member 12 are connected to each other using a connection section 15 such as stitches provided above the female surface fastener 14. In other words, as will be described below, the outer member 11 and the backing member 12 are connected to each other in a part other than the female surface fastener 14 which is a part of the backing member 12, to which the electrode unit 20 is attached.

As will be described below, the electrode-side male surface fastener 26 of the electrode unit 20 is attached to the female surface fastener 14. It is assumed that the closest part in a part in which the outer member 11 and the backing member 12 are connected to each other is the female surface fastener 14. The connection section 15 is away from the female surface fastener 14 and is preferably 1 cm or more away therefrom.

The wiring section 40 is a so-called flat cable. The wiring section 40 has a constitution in which a plurality of core wires (electrical wires) 43 are sandwiched between a first coating layer 41 and a second coating layer 42 which are formed of polyethylene terephthalate (PET) films having electrical insulation. The first coating layer 41 is formed on one side of each of the plurality of core wires 43 and the second coating layer 42 is formed on the other side thereof. The plurality of core wires 43 are electrically insulated from each other. The plurality of core wires 43 can be formed by printing a silver paste on the first coating layer 41.

The core wires 43 are formed of metals and do not have insulating coatings. The coating layers 41 and 42 insulate the core wires 43 from the outside.

The second coating layer 42 is not provided on an end portion 40a of the wiring section 40 and the plurality of core wires 43 are exposed to the other side. Note that, in FIG. 3, the end portion 40a of the wiring section 40 is hatched.

The end portion 40a of the wiring section 40 is inserted into the accommodation section 27 of the electrode unit 20. The end portion 40a of the wiring section 40 is a region in a certain range from an end of the wiring section 40 in a longitudinal direction of the wiring section 40, which is inserted into the accommodation section 27 of the electrode unit 20.

The width of an end of the end portion 40a of the wiring section 40 is shorter than the distance L1 of the accommodation section 27. The width of the end portion 40a of the wiring section 40 narrows toward the end thereof.

As shown in FIG. 1, a wiring-side male surface fastener (a second locked section) 45 locked to be attached to and detached from the female surface fastener 14 is fixed to a part closer to a central part of the wiring section 40 in a longitudinal direction of the wiring section 40 than the end portion 40a using an adhesive or the like. In other words, the wiring-side male surface fastener 45 is fixed to the core wires 43 via the coating layers 41 and 42. The wiring-side male surface fastener 45 has the same constitution as the electrode-side male surface fastener 26.

In this example, as shown in FIG. 1, the wiring section 40 is inserted into the accommodation section 27 so that the core wires 43 of the end portion 40a are on the sandwiched layer 22 side. The end portion 40a of the wiring section 40 is sandwiched by the conductive layer 21 and the sandwiched layer 22. When the end portion 40a of the wiring section 40 is inserted into the accommodation section 27, the core wires 43 come into contact with the sandwiched layer 22 and the core wires 43 of the wiring section 40 are electrically connected to the conductive layer 21 via the sandwiched layer 22. Note that the core wires 43 do not come into contact with the conductive layer 21.

A measuring device D shown in FIG. 1 is connected to an end portion of the wiring section 40 on an opposite side from the end portion 40a.

The measuring device D has a known constitution capable of processing an electric biological signal emitted by the user P.

For example, the measuring device D is held in an accommodation section 11a such as a pocket provided in the outer member 11. The measuring device D may be held in an accommodation section provided in the backing member 12, a waist bag attached to the user P, or the like.

An action of the wearable electrode 1 configured as described above will be described below.

The user P performs washing or the like of the undergarment 10 obtained by removing the electrode unit 20 and the wiring section 40.

The end portion 40a of the wiring section 40 is inserted into the accommodation section 27 of the washed electrode unit 20. The pair of connection section 23 and 24 are formed to extend in the reference direction X so that the end portion 40a of the wiring section 40 is inserted in the reference direction X. The distance L1 between the connection section 23 and 24 on the first side X1 in the reference direction X is shorter than the distance L2 on the second side X2. For this reason, the end portion 40a of the wiring section 40 inserted into the electrode unit 20 on the first side X1 in the reference direction X is sandwiched by the connection section 23 and 24 in the intersecting direction Y.

The core wires 43 of the wiring section 40 come into contact with the sandwiched layer 22. The core wires 43 of the wiring section 40 are electrically connected to the conductive layer 21 via the sandwiched layer 22. The position of the end portion 40a of the wiring section 40 with respect to the electrode unit 20 is maintained due to a frictional force occurring between the conductive layer 21 and the sandwiched layer 22 and the end portion 40a of the wiring section 40.

The electrode-side male surface fastener 26 of the electrode unit 20 and the wiring-side male surface fastener 45 of the wiring section 40 are locked to the female surface fastener 14 of the undergarment 10. The position of the end portion 40a of the wiring section 40 with respect to the electrode unit 20 is more reliably held by performing such locking in this manner.

The electrode unit 20 is disposed at a position at which it faces the chest P1 of the user P when the user P is clothed in the wearable electrode 1.

When the user P is clothed in the wearable electrode 1, the conductive layer 21 of the electrode unit 20 comes into contact with the skin of the chest P1 of the user P. Since the conductive layer 21 is easily deformed, the conductive layer 21 is easily deformed in accordance with a shape of the chest P1 and thus a biological signal emitted by the user P is easily acquired using the conductive layer 21.

The biological signal acquired using the conductive layer 21 of the electrode unit 20 is transmitted from the conductive layer 21 to the sandwiched layer 22 having a small resistivity and then transmitted from the sandwiched layer 22 to the measuring device D via the plurality of core wires 43.

When the measuring device D starts up, measurement of biological signals of electrocardiographic waveforms or the like is started. The user P performs an operation such as walking while measuring a biological signal.

The outer member 11 of the undergarment 10 moves along with the user P's motion in some cases. Since the connection section 15 is away from the female surface fastener 14 of the backing member 12, movement of the outer member 11 is suppressed from being transferred to the female surface fastener 14 of the backing member 12. For this reason, a state in which the conductive layer 21 of the electrode unit 20 comes into contact with the chest P1 of the user P is maintained.

As described above, according to the wearable electrode 1 of the embodiment, when the outer member 11 of the undergarment 10 worn by the user P moves, since the female surface fastener 14 and the connection section 15 are provided in different parts of the backing member 12, the movement of the outer member 11 is hardly transmitted to the electrode unit 20 via the connection section 15. Therefore, movement of the electrode unit 20 can be suppressed.

The distance L1 between the connection section 23 and 24 on the first side X1 in the reference direction X is shorter than the distance L2 on the second side X2. Therefore, the end portion 40a of the wiring section 40 inserted into the electrode unit 20 on the first side X1 in the reference direction X is sandwiched by the connection section 23 and 24 in the intersecting direction Y and thus the wiring section 40 can be reliably connected to the electrode unit 20.

The wiring section 40 is reliably connected to the electrode unit 20 so that the wiring section 40 does not deviate with respect to the electrode unit 20, the wiring section 40 is less likely to fall off, and thus noise in the acquired biological signal is reduced.

The conductive layer 21 is formed of a conductive fiber layer, and the sandwiched layer 22 is formed of a metal and is in contact with the conductive layer 21. For this reason, the conductive layer 21 is easily deformed in accordance with the shape of the chest P1 so that a biological signal from the chest P1 can be reliably acquired by the conductive layer 21. Moreover, even when the resistivity of the conductive layer 21 is relatively large, the biological signal acquired by the conductive layer 21 can be reliably transmitted to the core wires 43 of the wiring section 40 via the sandwiched layer 22 having a relatively small resistivity.

The female surface fastener 14 is fixed to the backing member 12, the electrode-side male surface fastener 26 is fixed to the electrode unit 20, and the wiring-side male surface fastener 45 is fixed to the wiring section 40. The male surface fasteners 45 and 26 are locked to the female surface fastener 14 so that the position of the end portion 40a of the wiring section 40 with respect to the electrode unit 20 can be more reliably held.

Although the embodiment of the present invention has been described in detail above with reference to the drawings, a specific constitution is not limited to such an embodiment and also includes a design or the like within the scope which does not depart from the gist of the present invention.

Figure 4:
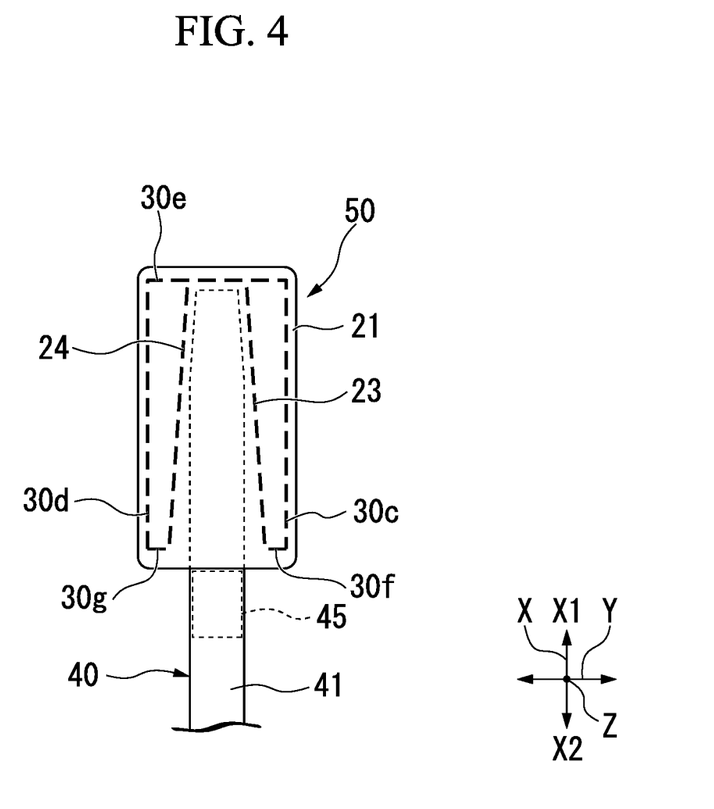
FIG. 4 is a bottom view of an electrode unit in a wearable electrode according to an embodiment of a modified example of the present invention.

For example, as shown in FIG. 4, an electrode unit 50 of a narrow width type may be used. A conductive layer 21, a sandwiched layer 22, and an electrode-side male surface fastener 26 in the electrode unit 50 have narrower widths than those of the above-described electrode unit 20. The electrode unit 50 may not include auxiliary connection sections 30a and 30b.

As described above, it is desirable to prepare electrode units of various specifications having different widths or lengths in advance in accordance with the body shape or the like of the user P.

In the embodiment, it is assumed that the wiring section 40 includes the plurality of core wires 43, but the wiring section 40 may include one core wire 43.

It is assumed that the sandwiched layer 22 is formed of a metal having conductivity. However, the sandwiched layer 22 may be formed of an insulating material. In this case, the wiring section 40 is inserted into the accommodation section 27 so that the core wires 43 of the end portion 40a are on the conductive layer 21 side. In other words, when the end portion 40a of the wiring section 40 is inserted into the accommodation section 27, the core wires 43 come into contact with the conductive layer 21.

The connection sections 23 and 24 and the auxiliary connection sections 30a to 30g are assumed to be configured using the stitches in the embodiment, but they may be configured using an adhesive such as hot melt.

It is assumed that the locking section corresponds to the female surface fastener 14, the first locked section corresponds to the electrode-side male surface fastener 26, and the second locked section corresponds to the wiring-side male surface fastener 45. However, it may be assumed that the locking section corresponds to a male surface fastener and the first and second locked sections correspond to female surface fasteners. It is assumed that the measuring device D configured to process a biological signal is electrically connected to the end portion of the wiring section 40. However, a device connected to the wiring section 40 is not limited thereto and may be, for example, a device capable of performing processing such as detection and display of a biological signal and a device configured to transmit a biological signal to an external device through wireless communication or the like.

INDUSTRIAL APPLICABILITY

According to the present invention, a wearable electrode in which movement of an electrode unit is suppressed even when a garment worn by a user moves can be provided.

REFERENCE SYMBOLS

1 Wearable electrode
10 Garment
11 Outer member
12 Backing member
14 Female surface fastener (locking section)
20, 50 Electrode unit
21 Conductive layer
21a One surface
22 Sandwiched layer
23, 24 Connection sections
26 Electrode-side male surface fastener (first locked section)
27 Accommodation section
43 Core wire
45 Wiring-side male surface fastener (second locked section)
L1,L2 Distance
P User (living body)
X Reference direction
X1 First side (one side)
X2 Second side (other side)
Y Intersecting direction

The invention claimed is:

1. A wearable electrode comprising:
a garment including an outer member and a backing member configured to cover at least a part of an inner surface of the outer member;
an electrode unit configured to come into contact with a living body clothed in the garment to acquire a biological signal emitted by the living body where the electrode unit is attached to a surface of the backing member which is opposite the surface of the backing member facing the outer member, wherein the electrode unit includes:
a conductive layer configured to acquire the biological signal;
a sandwiched layer disposed on and in contact with one surface of the conductive layer; and
a pair of connection sections configured to connect the conductive layer and the sandwiched layer by means of stitched threads, where the pair of connection sections extend in a reference direction along the one surface and are disposed along the one surface away from each other in a direction intersecting the reference direction;

an accommodation section formed by a part between the conductive layer and the sandwiched layer and configured to removably receive a core wire, wherein the core wire inserted into the accommodation section; and wherein the outer member and the backing member are connected to each other by stitches, such that the stitches are spatially separated from the electrode unit and disposed vertically from the electrode unit when the garment is being worn by the living body.

2. The wearable electrode according to claim 1, wherein a distance between the pair of connection sections in the reference direction on a first side is shorter than a distance between the pair of connection sections in the reference direction on a second side.

3. The wearable electrode according to claim 1, wherein the conductive layer is formed of a fiber structure impregnated with a conductive polymer, and the sandwiched layer is formed of a metal.

4. The wearable electrode according to claim 1, wherein:
a locking section is fixed to the backing member;
a first locked section that can be attached to and can be detached from the locking section is fixed to the electrode unit; and
a second locked section that can be attached to and can be detached from the locking section is fixed to the core wire.

5. The wearable electrode according to claim 1, wherein the stitches are spatially separated from the electrode unit by 1 cm or more.

* * * * *

UNITED STATES PATENT AND TRADEMARK OFFICE
CERTIFICATE OF CORRECTION

PATENT NO. : 10,835,141 B2
APPLICATION NO. : 15/577696
DATED : November 17, 2020
INVENTOR(S) : Shingo Tsukada et al.

It is certified that error appears in the above-identified patent and that said Letters Patent is hereby corrected as shown below:

On the Title Page

(73) Assignee
"NIPPON TELEGRAPH AND TELEPHONE CORPORATION , Tokyo (JP)" should be -- NIPPON TELEGRAPH AND TELEPHONE CORPORATION, Tokyo (JP); TORAY INDUSTRIES, INC., Tokyo (JP) --

Signed and Sealed this
Seventh Day of September, 2021

Drew Hirshfeld
*Performing the Functions and Duties of the*
*Under Secretary of Commerce for Intellectual Property and*
*Director of the United States Patent and Trademark Office*